United States Patent [19]

Seybold et al.

[11] Patent Number: 4,486,221
[45] Date of Patent: Dec. 4, 1984

[54] THIAZOLO[2,3-b]QUINAZOLONES AND THEIR USE FOR INFLUENCING PLANT GROWTH

[75] Inventors: Guenther Seybold, Neuhofen; Bruno Wuerzer, Otterstadt, both of Fed. Rep. of Germany

[73] Assignee: BASF Aktiengesellschaft, Fed. Rep. of Germany

[21] Appl. No.: 435,368

[22] Filed: Oct. 20, 1982

[30] Foreign Application Priority Data

Oct. 28, 1981 [DE] Fed. Rep. of Germany ....... 3142727

[51] Int. Cl.³ .................. A01N 43/90; C07D 513/04
[52] U.S. Cl. .................................... 71/90; 544/115; 544/250
[58] Field of Search ................... 544/250, 115; 71/90

[56] References Cited

U.S. PATENT DOCUMENTS

| | | | |
|---|---|---|---|
| 4,083,980 | 4/1978 | Schromm et al. | 424/251 |
| 4,168,380 | 9/1979 | LeMahieu | 544/250 |
| 4,282,360 | 8/1981 | LeMahieu | 544/250 |

FOREIGN PATENT DOCUMENTS

| | | | |
|---|---|---|---|
| 2393001 | 2/1979 | France | 424/251 |
| 005995 | 1/1979 | Japan | 71/90 |
| 1242863 | 8/1971 | United Kingdom | 544/250 |

OTHER PUBLICATIONS

Wagner, et al., Pharmazie, vol. 34, No. 4, 209–213, (1979).
Singh, et al., Chemical Abstracts, vol. 71, 101814q, (1969).
Modi, et al., Chemical Abstracts, vol. 73, 130960f, (1970).
Aktieselskabet Pharmica, Chemical Abstracts, vol. 75, 129827c, (1971).
Singh, et al., Chemical Abstracts, vol. 76, 140707e, (1972).
Gakhar, et al., Chemical Abstracts, vol. 79, 137084f, (1973).
Kishida, et al., Chemical Abstracts, vol. 83, 114460u, (1975).
Singh, et al., Chemical Abstracts, vol. 90, 137754b, (1979).

Primary Examiner—Nicholas S. Rizzo
Assistant Examiner—Diana G. Rivers
Attorney, Agent, or Firm—Keil & Weinkauf

[57] ABSTRACT

Thiazolo[2,3-b]quinazolones of the formula

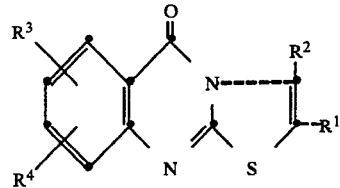

where $R^1$, $R^2$, $R^3$ and $R^4$ have the meanings given in the description, are used for influencing plant growth and for controlling undesirable plant growth.

9 Claims, No Drawings

THIAZOLO[2,3-B]QUINAZOLONES AND THEIR USE FOR INFLUENCING PLANT GROWTH

The present invention relates to thiazolo[2,3-b]quinazolones, herbicides and agents for influencing plant growth, which contain these compounds as active ingredients, and a process for influencing and controlling plant growth using these compounds.

Thiazolo[2,3-b]quinazolones which have antibacterial and pharmaceutical action have been disclosed (J. Sci. Ind. Res. (1958) 17 B, 120–123, and German Laid-Open Application DOS No. 2,557,425).

We have found that thiazolo[2,3-b]quinazolones of the formula

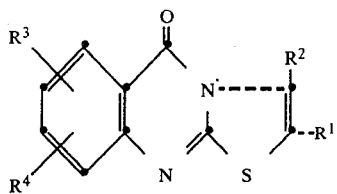

where $R^1$ and $R^2$ independently of one another are each hydrogen, halogen, nitro, cyano, alkyl, haloalkyl, cycloalkyl, alkoxy, alkylthio, thiophenyl, amino, alkylamino, dialkylamino, aminoalkyl, alkylaminoalkyl, dialkylaminoalkyl, alkanoylamino, haloalkanoylamino, carboxyl, carbamyl, dialkylcarbamido, alkoxycarbonyl, alkoxycarbonylalkyl, unsubstituted or alkoxy-substituted alkoxycarbonyl, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, di(hydroxyalkyl)-aminosulfonyl, morpholinylsulfonyl, alkylsulfonylamino, alkoxycarbonylalkylamino, or are each phenyl which is unsubstituted or substituted by halogen, alkoxy or carboxyalkoxy, or are each hetaryl which is unsubstituted or substituted by halogen or alkyl, and $R^3$ and $R^4$ independently of one another are each hydrogen, halogen, nitro, cyano, alkyl, haloalkyl, cycloalkyl, alkoxy, alkylthio, thiophenyl, amino, alkylamino, dialkylamino, aminoalkyl, alkylaminoalkyl, dialkylaminoalkyl, alkanoylamino, haloalkanoylamino, carboxyl, carbamyl, dialkylcarbamido, alkoxycarbonyl, alkoxycarbonylalkyl, unsubstituted or alkoxy-substituted alkoxycarbonyl, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, di-(hydroxyalkyl)aminosulfonyl, morpholinylsulfonyl, alkylsulfonylamino, alkoxycarbonylalkylamino, N-(ω-dialkylaminoalkyl)-aminosulfonyl or N-(ω-sulfoalkyl)-aminosulfonyl, with the proviso that $R^3$ is fluorine, nitro, cyano, alkyl of 2 to 9 carbon atoms, haloalkyl, cycloalkyl, alkoxy of 4 to 9 carbon atoms, alkylthio, thiophenyl, amino, alkylamino, dialkylamino, alkanoylamino, haloalkanoylamino, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, di-(hydroxyalkyl)aminosulfonyl, morpholinylsulfonyl, alkylsulfonylamino or alkoxycarbonylalkylamino, and $R^4$ has the above meanings, when $R^1$ is hydrogen, methyl, ethyl, halomethyl, aminomethyl, alkylaminomethyl, dialkylaminomethyl or alkoxycarbonyl and $R^2$ is hydrogen, methyl or ethyl, or phenyl which is unsubstituted or substituted by halogen, alkoxy or carbonylalkoxy, and their addition salts with acids, possess herbicidal and growth-influencing properties.

$R^1$, $R^2$, $R^3$ and $R^4$ in formula I are each hydrogen, halogen, eg. fluorine, chlorine, bromine or iodine, nitro, cyano, alkyl of 1 to 12, preferably 1 to 9, in particular 1 to 4, carbon atoms, eg. methyl, ethyl, n-propyl, isopropyl, n-butyl, i-butyl, sec.-butyl or tert.-butyl, haloalkyl of 1 to 4 carbon atoms, eg. chloromethyl, fluoromethyl, difluoromethyl, trichloromethyl, trifluoromethyl, pentafluoroethyl, 2-chloro-1,1,2,2-tetrafluoroethyl or nonafluoro-n-butyl, cycloalkyl of 3 to 6 carbon atoms, eg. cyclopropyl, cyclopentyl or cyclohexyl, alkoxy or alkylthio, each of 1 to 9, preferably 1 to 6, in particular 1 to 4, carbon atoms, eg. methoxy, methylthio, ethylthio, n-propylthio, ethoxy, n-butoxy, n-butylthio, isopropoxy or tert.-butoxy, thiophenyl, amino, alkyl- or dialkylamino where alkyl is of 1 to 4 carbon atoms, eg. methylamino, dimethylamino, n-butylamino, diethylamino, isopropylamino or methylethylamino, aminoalkyl, alkylaminoalkyl or dialkylaminoalkyl where alkyl is of 1 to 4 carbon atoms in each case, eg. aminomethyl, methylaminomethyl, dimethylaminomethyl, aminoethyl, methylaminoethyl or dimethylaminoethyl, alkanoylamino or haloalkanoylamino of 2 to 5 carbon atoms, eg. acetylamino, chloroacetylamino, trifluoroacetylamino, propionylamino or 2-chloropropionylamino, carboxyl, carbamyl, dialkylcarbamido where alkyl is of 1 to 4 carbon atoms, eg. N,N-dimethylcarbamido, N,N-diethylcarbamido or N,N-di-n-butylcarbamido, alkoxycarbonyl of 2 to 5 carbon atoms, eg. methoxycarbonyl, ethoxycarbonyl, n-propoxycarbonyl, tert.-butoxycarbonyl or isobutoxycarbonyl, alkoxycarbonylalkyl of 3 to 6 carbon atoms, eg. methoxycarbonylmethyl, ethoxycarbonylmethyl or n-butoxycarbonylmethyl, unsubstituted or alkoxy-substituted alkoxycarbonyl of 2 to 6 carbon atoms, eg. methoxycarbonyl, ethoxycarbonyl, n-propoxycarbonyl, n-butoxycarbonyl, isopropoxycarbonyl, 2-methoxyethoxycarbonyl, ethoxymethoxycarbonyl or 2-ethoxyethoxycarbonyl, sulfo, sulfino, alkylsulfonyl or alkylsulfinyl of 1 to 4 carbon atoms, eg. methylsulfonyl, methylsulfinyl, isopropylsulfonyl, n-propylsulfinyl, n-butylsulfonyl or n-butylsulfinyl, chlorosulfonyl, phenylsulfonyl, sulfamyl, alkylaminosulfonyl or alkylaminosulfinyl of 1 to 4 carbon atoms, eg. methylaminosulfonyl, methylaminosulfinyl, isopropylaminosulfonyl, n-butylaminosulfonyl or n-butylaminosulfinyl, hydroxyalkyl- or di-(hydroxyalkyl)-aminosulfonyl where hydroxyalkyl is of 1 to 4 carbon atoms, eg. 2-hydroxyethylaminosulfonyl or di-(2-hydroxyethyl)-aminosulfonyl, alkylsulfonylamino of 1 to 4 carbon atoms, eg. methylsulfonylamino, isopropylsulfonylamino or isobutylsulfonylamino, alkoxycarbonylalkylamino of 3 to 6 carbon atoms, eg. 2-methoxycarbonylethylamino or 2-n-butoxycarbonylethylamino, N-(ω-dialkylaminoalkyl)-aminosulfonyl where alkyl is of 1 to 4 carbon atoms, in particular N-(2-dialkylaminoethyl)-aminosulfonyl, eg. N-(2-diethylaminoethyl)-aminosulfonyl or N-(2-dimethylaminoethyl)-aminosulfonyl, or N-(ω-sulfoalkyl)-aminosulfonyl, eg. N-(2-sulfoethyl)-aminosulfonyl, or are each phenyl which is unsubstituted or substituted by halogen, alkoxy or carboxyalkoxy of not more than 5 carbon atoms, eg. phenyl, 4-chlorophenyl, 4-methoxyphenyl, 4-carboxymethoxyphenyl, 4-(2-carboxyethoxy)-phenyl or 3,5-dichlorophenyl, or are each hetaryl which is unsubstituted or substituted by halogen or alkyl of not more than 4 carbon atoms, eg. thien-2-yl, thiazol-2-yl, fur-2-yl, benzimidazol-2-yl, 2-chlorothien-4-yl, 2-methylthien-4-yl or 1-methylbenzimidazol-2-yl.

Compounds of the formula I, where $R^1$ is hydrogen, halogen, alkyl of 1 to 4 carbon atoms or alkoxycarbonyl of 2 to 5 carbon atoms, $R^2$ is hydrogen, chlorine, alkyl of 1 to 4 carbon atoms or alkoxycarbonyl of 2 to 5 carbon atoms, $R^3$ is fluorine or sulfo and $R^4$ is hydrogen, and addition salts of these compounds with acids, are preferred. Among these, particularly preferred compounds are those in which $R^3$ is in the 6-position and is fluorine, and those in which $R^3$ is in the 7-position and is sulfo.

The thiazolo[2,3-b]quinazolones of the formula I are obtained by reacting an anthranilic acid derivative of the formula

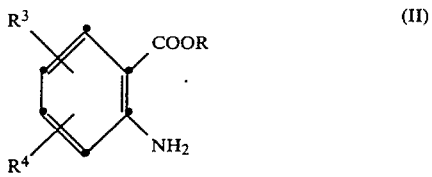

where R is hydrogen or alkyl, preferably of 1 to 4 carbon atoms, and $R^3$ and $R^4$ have the above meanings, with a thiocyanate derivative of the formula

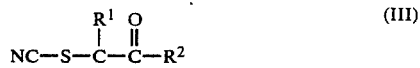

where $R^1$ and $R^2$ have the above meanings, or with a thiazole derivative of the formula

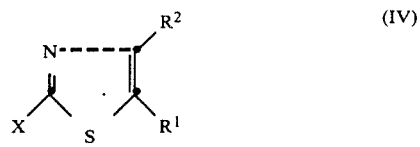

where X is fluorine, chlorine, bromine, alkylsulfonyl or arylsulfonyl and $R^1$ and $R^2$ have the above meanings.

The condensation of the anthranilic acid derivative of the formula II with the thiocyanate derivative of the formula III is preferably carried out in an aqueous medium in the presence of a strong mineral acid, eg. hydrochloric acid, hydrobromic acid or sulfuric acid. The starting materials are preferably employed in about stoichiometric amounts, although an excess of one or other of the reactants has no adverse effect on the course of the reaction. The reaction temperature may be from 40° to 150° C., preferably from 60° to 100° C. The acid is employed in an amount of from 1 to 2 mole equivalents, based on the amount of anthranilic acid derivative of the formula II.

The reaction of the anthranilic acid derivative of the formula II with the thiazole derivative of the formula IV is carried out at from 100° to 200° C., preferably from 130° to 160° C. The reactants are likewise employed in about stoichiometric amounts, but it is not necessary to add an acid. The reaction can be carried out in the presence or absence of a solvent, suitable solvents being halohydrocarbons, eg. dichlorobenzene and trichlorobenzene, polyhydric alcohols, eg. glycol, ethylglycol and butylglycol, esters, eg. methylglycol acetate, and dimethylformamide, as well as mixtures of these. The reaction is preferably carried out in the ab-sence of a solvent. In formula IV, X is preferably methylsulfonyl.

Some of the anthranilic acid derivatives of the formula II, thiocyanate derivatives of the formula III and thiozole derivatives of the formula IV, which are employed as starting materials, are known; they can be prepared by methods similar to those conventionally used (J. Am. Chem. Soc. 74 (1952), 1719, and Proc. Ind. Acad. Sci. 22A (1945), 343).

The addition salts of the thiazolo[2,3-b]quinazolones of the formula I with acids are obtained by protonation with the appropriate acid in the presence of an inert solvent, eg. tetrahydrofuran, dioxane, tert.-butyl methyl ether, methylene chloride or acetonitrile.

Examples of acids which may be used to form the corresponding salts are inorganic acids, eg. hydrochloric acid, hydrobromic acid, hydrofluoric acid, sulfuric acid, perchloric acid or phosphoric acid, and organic acids, eg. trichloroacetic acid, trifluoroacetic acid, dichloroacetic acid or monochloroacetic acid.

EXAMPLE 1

11.5 parts of acetonyl thiocyanate were added to 16.9 parts of methyl 6-fluoroanthranilate in 90 parts of water and 12 parts of concentrated hydrochloric acid, and the mixture was heated at 80° C. for 4 hours. The 18 parts of 3-methyl-6-fluoro-5H-thiazolo[2,3-]quinazolin-5-one formed were filtered off under suction and dried; melting point: 251°–253° C.

Analysis: Calculated: C 56.40, H 2.99, N 11.96, S 13.67, F 8.11. Found: C 56.4, H 3.2, N 12.3, S 13.7, F 8.2.

EXAMPLE 2

11.7 parts of the thiazoloquinazolone prepared as in Example 1 were dissolved in 80 parts of hot tetrahydrofuran, and 17.2 parts of 47% strength hydrobromic acid were added to the solution. The precipitate was filtered off under suction and dried. 13 parts of 3-methyl-6-fluoro-5H-thiazolo[2,3-b]quinazolin-5-one hydrobromide of melting point 284° C. were obtained.

Analysis: Calculated: Br 25.4. Found: Br 24.8.

The following thiazolo[2,3-b]quinazolones of the formula I may be prepared by procedures similar to those described in Examples 1 and 2:

| Example No. | $R^1$ | $R^2$ | $R^3$ | $R^4$ | Melting point [°C.] |
|---|---|---|---|---|---|
| 3 | H | CH₃ | 6-Cl | H | |
| 4 | H | CH₃ | H | 9-Cl | 221 |
| 5 | H | CH₃ | 7-CH₃ | H | 180 |
| 6 | H | CH₃ | 7-CH₃ | H (.HBr) | >300 |
| 7 | CH₃ | CH₃ | 6-F | H (.H₂SO₄) | >300 |
| 8 | H | CH₃ | 7-NO₂ | H | 308 |
| 9 | H | —CH₂COOC₂H₅ | H | H | 134–136 |
| 10 | H | —CH₂COOC₂H₅ | 6-F | H | >300 |
| 11 | H | —CH₂COOH | H | H | |
| 12 | H | thien-2-yl | H | H | 271–274 |
| 13 | H | CH₃ | 7-NH₂ | H | 249 |
| 14 | H | C₂H₅ | H | H | 185 |

EXAMPLE 15

15 parts of 2-methyl-5H-thiazolo[2,3-b]quinazolin-5-one were introduced slowly into 70 parts of chlorosulfonic acid, at 20°–30° C. Stirring was continued for 12 hours, and the 2-methyl-7-chlorosulfonyl-5H- thiazolo[2,3-b]quinazolin-5-one formed was precipitated with ice water.

Melting point: 206°–209° C.

Analysis: Calculated: Cl 11.3. Found: Cl 10.7.

EXAMPLE 16

16 parts of the sulfochloride prepared as described in Example 15, in 200 parts of toluene, and 20 parts of butylamine were stirred for 2 hours at 40° C. The solvent was stripped off and water was added, and the precipitate which separated out was then filtered off under suction and dried. 14 parts of 3-methyl-7-(n-butylaminosulfonyl)-5H-thiazolo[2,3-b]quinazolin-5-one of melting point 165°–167° C. were obtained.

The following thiazolo[2,3-b]quinazolones of the formula I may be obtained by procedures similar to those described in Examples 15 and 16:

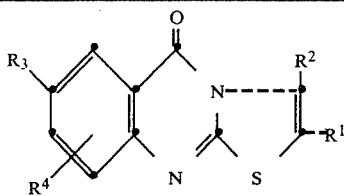

| Example No. | $R^1$ | $R^2$ | $R^3$ | $R^4$ | Melting point [°C.] |
|---|---|---|---|---|---|
| 17 | H | $CH_3$ | $(HOC_2H_4)_2N-SO_2-$ | H | 230 |
| 18 | H | $CH_3$ | O⟨⟩N—$SO_2-$ | H | 266 |
| 19 | H | $CH_3$ | $(CH_3)_2N-SO_2-$ | H | 255 |
| 20 | H | $CH_3$ | $(C_2H_5)_2N-CH_2-CH_2-NH-SO_2-$ | H | 95–100 |
| 21 | $CH_3$ | $CH_3$ | $ClO_2S-$ | H | 214 |
| 22 | $CH_3$ | $CH_3$ | $CH_3-NH-SO_2-$ | H | |
| 23 | $CH_3$ | $C_2H_5$ | $HOC_2H_4NH-SO_2-$ | H | 210 |
| 24 | $CH_3$ | $C_2H_5$ | $HO_3S-C_2H_4NH-SO_2-$ | H | 305–307 |

EXAMPLE 25

406 parts of the sulfochloride prepared as described in Example 15, in 400 parts of water, were hydrolyzed at pH 9, using sodium hydroxide solution. After acidification of the mixture with hydrochloric acid, the 3-methyl-7-sulfo-5H-thiazolo[2,3-b]quinazolin-5-one was precipitated and was filtered off under suction and dried; melting point 300° C.

| Example No. | $R^1$ | $R^2$ | $R^3$ | $R^4$ | Melting point [°C.] |
|---|---|---|---|---|---|
| 26 | $CH_3$ | $CH_3$ | $7-SO_3H$ | H | >300 |
| 27 | H | $CH_3$ | 6-F | $7-SO_3H$ | >300 |
| 28 | H | H | $7-SO_3H$ | H | >300 |
| 29 | $CH_3$ | $C_2H_5$ | $7-SO_3H$ | H | >300 |
| 30 | H | $CH_3$ | $7-SO_3H$ | 9-Cl | >300 |
| 31 | H | $CH_3$ | $7-SO_3H$ | 9-F | >300 |
| 32 | Cl | $CH_3$ | $7-SO_3H$ | H | >300 |
| 33 | COOH | $CH_3$ | $7-SO_3H$ | H | >300 |

EXAMPLE 34

31.4 parts of the sulfochloride prepared as described in Example 15 were introduced into a solution of 18 parts of sodium sulfite in 125 parts of water at 40° C., and the pH of the mixture was brought to 7 with sodium carbonate. Thereafter, the mixture was stirred for a further 5 hours at 60° C. The 3-methyl-7-sulfino-5H-thiazolo[2,3-b]quinazolin-5-one was isolated by acidifying the mixture with sulfuric acid. Melting point: (slow decomposition) >300° C.

The following thiazolo[2,3-b]quinazolones of the formula I can be prepared by a procedure similar to that described in Example 34:

| Example No. | $R^1$ | $R^2$ | $R^3$ | $R^4$ | Melting point [°C.] |
|---|---|---|---|---|---|
| 35 | $CH_3$ | $CH_3$ | $7-SO_2H$ | H | >300 |
| 36 | H | $CH_3$ | 6-F | $7-SO_2H$ | >300 |
| 37 | H | H | $7-SO_2H$ | H | >300 |
| 38 | $CH_3$ | $C_2H_5$ | $7-SO_2H$ | H | >300 |
| 39 | H | $CH_3$ | $7-SO_2H$ | 9-Cl | >300 |
| 40 | H | $CH_3$ | $7-SO_2H$ | 9-F | >300 |
| 41 | H | $CH_3$ | 6-Cl | $7-SO_2H$ | >300 |

EXAMPLE 42

25.4 parts of methyl 6-fluoroanthranilate and 18 parts of 2-chlorothiazole were heated to 150° C., and the methanol formed was distilled off over a bridge. The reaction was complete after 2 hours. The solid residue was neutralized, and recrystallized from isopropanol. 30 parts of 6-fluoro-5H-thiazolo[2,3-b]quinazolin-5-one of melting point 205°–207° C. were obtained.

The following thiazolo[2,3-b]-quinazolones of the formula I may be prepared analogously to Example 42:

| Ex. no. | $R^1$ | $R^2$ | $R^3$ | $R^4$ | M.p. (°C.) |
|---|---|---|---|---|---|
| 43 | H | H | 6-F | H (x HBr) | 290 |
| 44 | H | H | H | 9-F (x $H_2SO_4$) | >300 |
| 45 | H | H | 6-F | H (x $H_2SO_4$) | >300 |

-continued

| Ex. no. | R$^1$ | R$^2$ | R$^3$ | R$^4$ | M.p. (°C.) |
|---|---|---|---|---|---|
| 46 | H | H | 7-Cl | H (x HClO$_4$) | >300 |
| 47 | —COOCH$_3$ | CH$_3$ | 6-F | H | |
| 48 | —COOCH$_3$ | CH$_3$ | H | 9-F | |
| 49 | Cl | H | H | H | |
| 50 | Cl | CH$_3$ | H | H | |
| 51 | F | CH$_3$ | H | H | |
| 52 | —COOCH$_3$ | —COOCH$_3$ | H | H | |
| 53 | H | —COOCH$_3$ | H | H ($\gamma_{20}$ = 1720 cm$^{-1}$) | |
| 54 | H | —COOH | H | H | |
| 55 | CN | CH$_3$ | H | H ($\gamma_{CN}$ = 2150 cm$^{-1}$) | |
| 56 | Cl | CH$_3$ | 6-F | H | |
| 57 | Cl | CH$_3$ | 6-Cl | H | |

The compounds of the formula I, or their addition salts with acids, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 6 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 16 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 10 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 23 is intimately mixed with 97 parts by weight of particulate kaolin. A dust is obtained containing 3% by weight of the active ingredient.

VII. 30 parts by weight of the compound of Example 45 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of the compound of Example 27 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents, may be applied pre- or (preferably) postemergence. The agents may be applied before the unwanted plants have germinated from seed or sprouted from vegetative plant parts, or they may be applied to the leaves of unwanted and crop plants. Preferably, the novel active ingredients are applied after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.05 to 15 kg/ha and more, but is preferably from 0.25 to 5 kg/ha. The higher application rates are particularly suitable for total elimination of vegetation.

The herbicidal and growth-regulating action of herbicidal agents containing compounds of the formula I is demonstrated in greenhouse experiments.

The vessels employed were plastic flowerpots having a volume of 300 cm$^3$, and which were filled with a sandy loam containing about 1.5% humus. Peat was added to rice (grown for the postemergence treatment) to ensure good growth. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was, for example, 2 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. The application rates for postemergence treatment varied from ingredient to ingredient, and were equivalent, for example, to 2.0 or 3.0 kg/ha active ingredient per hectare.

The pots were set up in the greenhouse—species from warmer areas at from 20° to 30° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were *Abutilon theophrasti, Amaranthus retroflexus, Avena sativa, Cassia tora, Chenopodium album, Daucus carota, Hordeum vulgare,* Ipomoea spp., *Lamium purpureum, Mercurialis annua, Nicandra physaloides, Oryza sativa, Rottboellia exaltata, Rumex obtusifolium, Sesbania exaltata,* Setaria spp., *Sida spinosa, Solanum nigrum, Veronica persica, Viola tricolor,* and *Zea mays.*

On preemergence application, for example compounds nos. 1 and 2 had a herbicidal action without damaging cereal species.

Compounds nos. 1, 2, 25, 28 and 42 combated, on postemergence application of, for instance, 2.0 and 3.0 kg/ha, unwanted plants in crops such as rice, oats and Indian corn.

In view of the good tolerance of the active ingredients and the many application methods possible, the compounds according to the invention, or agents containing them, may be used in a large number of crop plants, apart from those used in the greenhouse experiments, for removing unwanted plant growth.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and |

-continued

| Botanical name | Common name |
| --- | --- |
|  | lawns |
| Daucus carota | carrots |
| Elais guineensis | oil palms |
| Fragaria vesca | strawberries |
| Glycine max | soybeans |
| Gossypium hirsutum | cotton |
| (Gossypium arboreum |  |
| Gossypium herbaceum |  |
| Gossypium vitifolium) |  |
| Helianthus annuus | sunflowers |
| Helianthus tuberosus |  |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum | tobacco |
| (N. rustica) |  |
| Olea europaea | olive trees |
| Oryza sativa | rice |
| Panicum miliaceum |  |
| Phaseolus lunatus | limabeans |
| Phaseolus mungo | mungbeans |
| Phaseolus vulgaris | snapbeans, green beans. dry beans |
| Pennisetum glaucum |  |
| Petroselinum crispum | parsley |
| spp. tuberosum |  |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna |  |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, wetting agents, spreader-stickers, and non-phytotoxic oils and oil concentrates may also be added.

We claim:

1. A thiazolo[2,3-b]-quinazolone of the formula

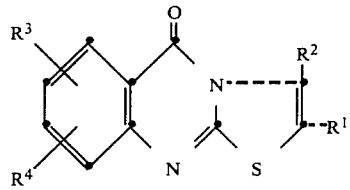

where $R^1$ and $R^2$ independently of one another are each hydrogen, halogen, nitro, cyano, alkyl of 1–12 carbons, haloalkyl of 1–4 carbons, cycloalkyl of 3–6 carbons, alkoxy of 1–9 carbons, alkylthio of 1–9 carbons, thiophenyl, amino or alkylamino, dialkylamino, aminoalkyl or alkylaminoalkyl in which alkyl is of 1–4 carbons, alkanoylamino or haloalkylanoylamino of 2–5 carbons, carbamyl, dialkylcarbamido in which the alkyls are of 1–4 carbons, alkoxycarbonyl of 2–5 carbons, alkoxycarbonylalkyl of 3–6 carbons, unsubstituted or alkoxy-substituted alkoxycarbonyl of 2–6 carbons, sulfo, sulfino, alkylsulfonyl of 1–4 carbons, alkylsulfinyl of 1–4 carbons, chlorosulfonyl, phenylsulfonyl, sulfamyl, alkylaminosulfinyl of 1–4 carbons, alkylaminosulfonyl of 1–4 carbons, hydroxyalkylaminosulfonyl of 1–4 carbons, di(hydroxyalkyl)-aminosulfonyl of 1–4 carbons, morpholinylsulfony, alkylsulfonylamino of 1–4 carbons, alkoxycarbonylalkylamino of 3–6 carbons, or are each thien-2-yl, thiazol-2-yl, fur-2-yl, benzimidazol-2-yl, 2-chlorothien-4-yl, 2-methylthien-4-yl or 1-methylbenzimidazol-2-yl, and $R^3$ and $R^4$ independently of one another are each hydrogen, halogen, nitro, cyano, alkyl of 1–12 carbons, haloalkyl of 1–4 carbons, cycloalkyl of 3–6 carbons, alkoxy of 1–9 carbons, thiophenyl, amino or alkylamino, dialkylamino, aminoalkyl, alkylaminoalkyl or dialkylaminoalkyl in which the alkyls are of 1–4 carbons, alkanoylamino or haloalkanoylamino of 2–5 carbons, carboxyl, carbamyl, dialkylcarbamido, alkoxycarbonyl of 2–5 carbons, alkoxycarbonylalkyl of 3–6 carbons, unsubstituted or alkoxy-substituted alkoxycarbonyl of 2–6 carbons, sulfo, sulfino, alkylsulfonyl of 1–4 carbons, chlorosulfonyl, phenylsulfonyl, sulfamyl, alkylaminosulfinyl of 1–4 carbons, alkylaminosulfonyl of 1–4 carbons, hydroxyalkylaminosulfonyl of 1–4 carbons, di-(hydroxyalkyl)-aminosulfonyl, morpholinylsulfonyl, alkylsulfonylamino of 1–4 cargons, alkoxycarbonylalkylamino of 1–4 carbons, N-(w-dialkylaminoalkyl)-aminosulfonyl where alkyl is of 1–4 carbons or N-(w-sulfoalkyl)-aminosulfonyl where alkyl is of 1–4 carbons, with the proviso that $R^3$ is fluorine, cyano, alkyl of 2 to 9 carbon atoms, haloalkyl of 1–4 carbons, cycloalkyl of 3–6 carbons, alkoxy of 4 to 9 carbons atoms, alkylthio of 1–4 carbons, thiophenyl, amino, alkylamino, dialkylamino, alkanoylamino, haloalkanoylamino, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, di-(hydroxyalkyl)-aminosulfonyl, morpholinylsulfonyl, alkylsulfonylamino or alkoxycarbonylalkylamino, and $R^4$ has the above meanings, when $R^1$ is hydrogen, methyl, ethyl, halomethyl, aminomethyl, alkylaminomethyl or alkoxycarbonyl and $R^2$ is hydrogen, methyl or ethyl alkoxy or carbonylalkoxy, or an acid addition salt thereof.

2. A thiazolo[2,3-b]-quinazolone of the formula

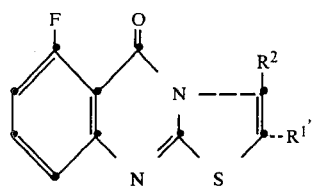

where $R^1$ is hydrogen, halogen, alkyl of 1 to 4 carbon atoms or alkoxycarbonyl of 2 to 5 carbon atoms, and $R^2$ is hydrogen, chloro, alkyl of 1 to 4 carbon atoms or alkoxycarbonyl of 2 to 5 carbon atoms, or an acid addition salt thereof.

3. A thiazolo[2,3-b]-quinazolone of the formula

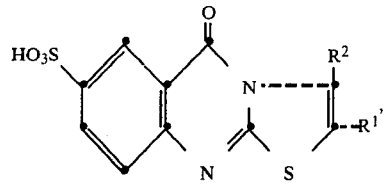

where $R^1$ is hydrogen, halogen, alkyl of 1 to 4 carbon atoms or alkoxycarbonyl of 2 to 5 carbon atoms, and $R^2$ is hydrogen, chloro, alkyl of 1 to 4 carbon atoms or alkoxycarbonyl of 2 to 5 carbon atoms, or an acid addition salt thereof.

4. 3-Methyl-6-fluoro-5H-thiazolo[2,3-b]-quinazolin-5-one.

5. 3-Methyl-7-fluoro-5H-thiazolo[2,3-b]-quinazolin-5-one.

6. A herbicide containing inert additives and a thiazolo[2,3-]-quinazolone of the formula I as claimed in claim 1, or an acid addition salt thereof.

7. An agent for influencing plant growth, containing inert additives and a thiazolo[2,3-b]-quinazolone of the formula I as set forth in claim 1 or an acid addition salt thereof.

8. A process for combating unwanted plant growth, wherein a thiazolo[2,3-b]-quinazolone of the formula I as set forth in claim 1, or an acid addition salt thereof, is allowed to act on the plants and/or their location.

9. A process for influencing plant growth, wherein a thiazolo[2,3-b]-quinazolone of the formula I as set forth in claim 1, or an acid addition salt thereof, is allowed to act on the plants and/or their location.

* * * * *